United States Patent [19]

Durden et al.

[11] Patent Number: 4,496,591
[45] Date of Patent: Jan. 29, 1985

[54] INSECTICIDAL BIS-CARBAMATE SULFIDES

[75] Inventors: John A. Durden, Raleigh; Themistocles D. J. D'Silva, Chapel Hill, both of N.C.

[73] Assignee: Union Carbide Corporation, Danbury, Conn.

[21] Appl. No.: 311,306

[22] Filed: Oct. 14, 1981

[51] Int. Cl.$^3$ .............................................. C07C 69/013
[52] U.S. Cl. .................................. 514/477; 260/453.3
[58] Field of Search ................... 260/453.3; 424/298, 424/300

[56] References Cited

U.S. PATENT DOCUMENTS

| | | | |
|---|---|---|---|
| 4,210,668 | 7/1980 | Hay | 260/453.3 |
| 4,216,147 | 8/1980 | Wolf | 260/453.3 |
| 4,330,674 | 5/1982 | Cheng | 260/453.3 |

*Primary Examiner*—Henry R. Jiles
*Attorney, Agent, or Firm*—Clement J. Vicari

[57] ABSTRACT

Bis-carbamoyl sulfide compounds exhibit exceptional broad spectrum pesticidal activity and increased residual pesticidal activity, coupled with extremely low phytotoxicity.

15 Claims, No Drawings

INSECTICIDAL BIS-CARBAMATE SULFIDES

BACKGROUND OF THE INVENTION

This invention relates to methods and compositions for controlling insect and nematode pests. In another aspect this invention relates to novel bis-carbamoyl sulfide compounds and to their production. Such compounds exhibit unexpectedly long soil residual activity.

U.S. patent application Ser. No. 636,623, filed Dec. 1, 1975 and Ser. No. 079,893 filed Sept. 28, 1979 disclose the use of asymmetrical bis-carbamate compounds as pesticides. In addition, U.S. Pat. No. 4,210,668, issued July 1, 1980, discloses insecticidal and nematicidal ester, thioester and amide derivatives of asymmetrical bis-carbamate compounds.

The novel compounds of the present invention exhibit increased soil residual activity for periods of up to eight weeks. This feature, coupled with such compounds' low phytotoxicity, results in the novel compounds having an ability to promote healthy crop growth correspondingly.

DESCRIPTION OF THE INVENTION

The compounds which are employed as the active ingredients in the pesticidal compositions of this invention are bis-carbamoyl sulfide compounds of the general formula:

$$\begin{array}{c} R_1 \\ \phantom{R_2S} \diagdown \\ R_2S \phantom{\diagdown} \end{array} C=N-O-\overset{O}{\underset{\|}{C}}-\overset{CH_3}{\underset{|}{N}}-S-\overset{CH_3O}{\underset{|}{N}}-\overset{}{\underset{\|}{C}}-O-\!\!\bigcirc\!\!\!\begin{array}{c}\\ \overset{O}{\underset{\|}{C}}-R_3 \\ R_5 \phantom{X} R_4\end{array} \quad (I)$$

wherein:

$R_1$ and $R_2$ independently are $C_{1-4}$ alkyl;

$R_3$ is hydrogen, hydroxyl, $C_{1-4}$ alkyl or a phenyl group; and $R_4$ and $R_5$ independently are hydrogen, $C_{1-4}$ alkyl or alkoxy.

The preferred compounds of this invention are those in which $R_1$ and $R_2$ are methyl, and $R_4$ and $R_5$ are hydrogen. Representative of such preferred compounds are:

(a) S-Methyl-N-[[[N'-[[N''-[(2-formylphenoxy)carbonyl]-N''-methylaminosulfenyl]]-N'-methylcarbamoyloxy]]]thioacetimidate.

$$CH_3-\underset{\underset{SCH_3}{|}}{C}=NO\overset{O}{\underset{\|}{C}}-\overset{CH_3}{\underset{|}{N}}-S-\overset{CH_3O}{\underset{|}{N}}-\overset{}{\underset{\|}{C}}-O-\!\!\bigcirc\!\!\text{-CHO}$$

(b) S-Methyl-N-[[[N'-[[N''-[(3-formylphenoxy)carbonyl]-N''-methylaminosulfenyl]]-N'-methylcarbamoyloxy]]]thioacetimidate.

$$CH_3-\underset{\underset{SCH_3}{|}}{C}=NO\overset{O}{\underset{\|}{C}}-\overset{CH_3}{\underset{|}{N}}-S-\overset{CH_3O}{\underset{|}{N}}-\overset{}{\underset{\|}{C}}-O-\!\!\bigcirc\!\!\text{-CHO}$$

(c) S-Methyl-N-[[[N'-[[N''-[(3-acetylphenoxy)carbonyl]-N''-methylaminosulfenyl]]-N'-methylcarbamoyloxy]]]thioacetimidate.

$$CH_3-\underset{\underset{SCH_3}{|}}{C}=NO\overset{O}{\underset{\|}{C}}-\overset{CH_3}{\underset{|}{N}}-S-\overset{CH_3O}{\underset{|}{N}}-\overset{}{\underset{\|}{C}}-O-\!\!\bigcirc\!\!\text{-COCH}_3$$

The compounds of this invention can be prepared conveniently by the methods shown in the following general reaction scheme:

$$A-OH + F-\overset{O}{\underset{\|}{C}}-\overset{CH_3}{\underset{|}{N}}-D \xrightarrow[\text{acceptor}]{\text{acid}} A-O-\overset{O}{\underset{\|}{C}}-\overset{CH_3}{\underset{|}{N}}-D$$

wherein A is:

$$\begin{array}{c}R_3\phantom{XX}O\\ \diagdown\phantom{X}\|\\ \phantom{XXX}C-\!\!\bigcirc\!\!\\ R_4\phantom{XX}R_5\end{array}$$

and D is: $-S-\overset{CH_3O}{\underset{|}{N}}-\overset{}{\underset{\|}{C}}-O-N=\underset{\underset{SR_2}{|}}{C}-R_1$ or wherein A is: $R_1-\underset{\underset{R_2S}{|}}{C}=N-$ and D is: $-S-\overset{CH_3O}{\underset{|}{N}}-\overset{}{\underset{\|}{C}}-O-\!\!\bigcirc\!\!\!\begin{array}{c}\\ \overset{O}{\underset{\|}{C}}-R_3 \\ R_5 \phantom{X} R_4\end{array}$ and $R_1$, $R_2$, $R_3$ $R_4$ and $R_5$ are as defined above.

One equivalent of an oxime or phenolic reactant is reacted with an appropriate carbamoyl fluoride reactant in the presence of one equivalent of an acid acceptor to produce the desired product. Preferably, such reaction is performed in the presence of an inert organic solvent.

The production of the intermediate carbamoyl fluoride reactants is described in U.S. patent application Ser. No. 192,601, filed on Sept. 30, 1980. Such production involves reacting hydrogen fluoride with an alkylisocyanate to form N-alkylcarbamoyl fluoride, which is then reacted with sulfur dichloride in the presence of an acid acceptor to produce a bis-fluorocarbamoyl sulfide compound. This bis-fluorocarbomoyl sulfide compound is then reacted with one equivalent of the appropriate oxime or phenolic reactant in the presence of an acid acceptor to produce the desired carbamoyl fluoride reactant.

The oxime and phenolic reactants are either commercially available or can be readily prepared by well known methods. For example, reacting an aldoxime of the formula $R_1$—CH=NOH with chlorine will produce an alkylhydroxamic acid chloride of the formula:

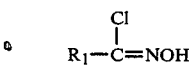

Reacting such alkylhydroxamic acid chloride with a mercaptan of the formula $R_2$—SH and a base will produce an alkylthiohydroximate of the formula:

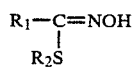

Phenolic reactants of the formula:

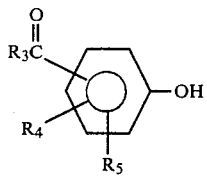

are available commercially or can be produced by well known methods.

The process is conducted in the presence of at least one equivalent of an acid acceptor. The acid acceptor employed can be either an organic or an inorganic base such as triethylamine, tetraethylenediamine, pyridine or sodium or potassium hydroxide. When an inorganic base is employed, a phase-transfer agent such as quarternary ammonium salts or crown ethers may also be used.

The reaction is normally carried out in the presence of an inert organic solvent. Illustrative of such inert solvents are aromatic solvents such as benzene, toluene, xylene and the like, ethers such as dioxane, tetrahydrofuran, ethyl ether, and the like; and chlorinated hydrocarbons such as methylene chloride and the like. Pyridine may also be used both as an acid acceptor and the reaction solvent.

Reaction temperatures are not critical in the conduct of this reaction and may range from ~ −50° C. to about 100° C. The reactions are preferably conducted at a temperature ranging from ~0° to about 40° C.

This reaction may also be carried out in two-phase systems such as an aqueous solution of an inorganic base as one phase and an aromatic solvent as the second phase using a quaternary ammonium salt as a phase transfer agent.

The following compounds are illustrative of the new compounds of this invention:

S-Isopropyl-N-[[[N'-[[N''-[(2-formyl phenoxy)carbonyl]-N''-methylaminosulfenyl]]-N'-methylcarbamoyloxy]]]thioacetimidate S-Ethyl-N-[[[N'-[[N''-[(2-hydroxycarbonylphenoxy)carbonyl]-N''-methylaminosulfenyl]]N'-methylcarbamoyloxy]]]thioacetimidate S-Methyl-N-[[[N'-[[N''-[2-butoxy-4-formylphenoxy)carbonyl]-N''-methylaminosulfenyl]]-N'-methylcarbamoyloxy]]]thioacetimidate S-Methyl-N-[[[N'-[[N''-[(2,6-di-tert-butyl-4-formylphenoxy)carbonyl]-N''-methylaminosulfenyl]]-N'-methylcarbamoyloxy]]]thioacetimidate S-Methyl-N-[[[N'-[[N''-[(3-acetylphenoxy)carbonyl]-N''-methylaminosulfenyl]]-N'-methylcarbamoyloxy]]]thioacetimidate S-Methyl-N-[[[N'-[[N''-[(4-hydroxycarbonylphenoxy)carbonyl]-N''-methylaminosulfenyl]]-N'-methylcarbamoyloxy]]]thioacetimidate The following specific examples are provided to illustrate the procedures used for the preparation of the compounds of this invention.

EXAMPLE I (COMPOUND 1)

Preparation of S-Methyl-N-[[[N'-[[N''-[(3-acetylphenoxy)carbonyl]-N''-methylaminosulfenyl]]-N'-methylcarbamoyloxy]]]-thioacetimidate

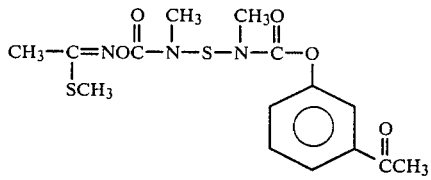

To a 3-neck flask equipped with a magnetic stirrer, a thermometer and a dropping funnel were added 3.5 g (0.013 m) of 1-methylthioacetaldehyde O-[N-(N'-methyl-N'-fluorocarbonylaminosulfenyl)-N-methylcarbamoyl]oxime, 1.76 g (0.013 m) of 3-hydroxyacetophenone and 50 ml of toluene. The mixture was warmed to 45° C. until the solution was homogeneous. The reaction mixture was cooled to 20° C. and 1.32 g (0.013 m) of triethylamine was added dropwise. After heating at 50° C. for 20 hours and standing at room temperature for 48 hours, the solution was diluted with water. The solid was collected and dried. Recrystallization from hexane-ethyl acetate afforded 2.1 g of a white solid. m.p. 98°–99.5° C.

Calcd. for $C_{15}H_{19}N_3O_5S_2$: C, 46.74; H, 4.97; N, 10.90. Found: C, 46.81; H, 5.04; N, 11.24.

EXAMPLE II (COMPOUND 4)

Preparation of S-Methyl-N-[[[N'-[[N''-[(4-hydroxycarbonylphenoxy)carbonyl]-N''-methylaminosulfenyl]]-N'-methylcarbamoyloxy]]]thioacetimidate

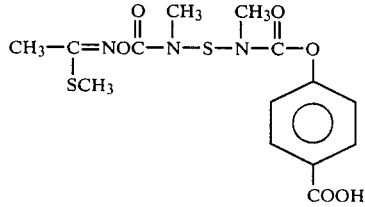

To a cooled solution of 3.5 g (0.013 m) of 1-methylthioacetaldehyde O-[N-(N'-methyl-N'-fluorocarbonylaminosulfenyl)-N-methylcarbamoyl]oxime, were added, with stirring, a solution of 1.79 g (0.013 m) of 4-hydroxybenzoic acid and 1.69 g (0.026 m) of potassium hydroxide in 10 ml of water. One drop of aliquat 336 (a phase transfer agent) was added and the mixture was stirred at ambient temperature for 16 hours. The toluene layer was separated and was washed twice with 50 ml of water. The combined water layers was acidified with dilute hydrochloric acid. The solid precipitate was filtered and dried. Weight of the product was 5.1 g. Recrystallization from ethyl acetate solution afforded 3.5 g of a white solid. m.p. 180°–183° C.

Calcd. for $C_{14}H_{17}N_3O_6S_2$: C, 43.40; H, 4.42; N, 10.84. Found: C, 43.43; H, 4.48; N, 10.67.

Compounds 2, 3, and 5–10 were prepared in a similar manner using one of the above procedures. See Table I below.

Selected species of the new compounds were evaluated to determine their pesticidal activity against nematodes and certain insects, including an aphid, a catapillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The concentrations in parts per million by weight employed in the tests described hereinbelow were obtained by appropriate dilutions of the stock suspension with water. The test procedures were as follows:

BEAN APHID FOLIAGE SPRAY TEST

Adults and nymphal stages of the bean aphid (Aphis fabae Scop.) reared on potted dwarf nasturtium plants at 68°–70° F. and 50±5 percent relative humidity, constituted the test insects. For testing purposes, the number of aphids per pot were standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound was also sprayed on infested plants. After spraying, the pots were placed on their sides on a sheet of white standard mimeograph paper which had been previously ruled to facilitate counting. Temperature and humidity in the test room during the 24 hour holding period were 68°–70° F. and 50±5 percent, respectively. Aphids which fell onto the paper and were unable to remain standing after being uprighted were considered dead. Aphids remaining on the plants were observed closely for movement and those which were unable to move the length of the body upon stimulation by prodding were considered dead.

SOUTHERN ARMYWORM LEAF SPRAY BAIT TEST

Larvae of the southern armyworm (Spodoptera eridania, (Cram.)), reared on Tendergreen bean plants at a temperature of 80±5° F. and a reative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet the plants to run-off. As a control, 100–110 milliliters of a water-acetone-emulsifier solution containing no test compound were also sprayed on infested plants. When dry, the paired leaves were separated and each one was placed in a 9 centimeter Petri dish lines with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead.

MEXICAN BEAN BEETLE LEAF SPRAY TEST

Fourth instar larvae of the Mexican bean beetle (Epilachna varivestis, Muls.), reared on Tendergreen bean plants at a temperature of 80±5° F. and 50±5° F. percent relative humdity, were the test insects.

The test compounds were formulated by diluting the stock suspension with water to give a suspension containing 500 parts of test compound per million parts of final formulation. Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet the plants to run-off. As a control, 100–110 milliliters of a water-acetone-emulsifier solution containing no test compound was also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5° F., for three days. Although the larvae could easily consume the leaf within 24 to 48 hours, no more food was added. Larvae which were unable to move the length of the body, even upon stimulation, were considered dead.

SOUTHERN ARMYWORK OVICIDE TEST

The test organism was the egg of the Southern armyworm (Spodoptera eridania (Cram.)) as obtained from adults reared on Tendergreen bean plants at a temperature of 80±5° F. and a relative humidity of 50±5 percent. The eggs were laid on freezer paper (Marlon 717, Copco paper) and then cut into small sections containing one or two egg masses.

The test compounds were formulated by diluting the stock suspension with water to give a suspension containing 500 parts of test compound per million parts of final formulation. The egg masses were then dipped until they were thoroughly wet (5–10 seconds). They were then placed on a paper towel face up and were allowed to dry for 15–30 minutes. The dry eggs were placed in a 15×60 mm petri dish containing a cotton dental wick saturated with a 5 percent sodium chloride solution to maintain a high level of humidity. The closed dishes were labeled and held at a temperature of 80±5° F. for four days. Larvae that emerged from the egg, even if dead at the time of observation, were recorded as hatched.

FLY BAIT TEST

Four to six day old adult house flies (*Musca domestica*, L.), reared according to the specifications of the Chemical Specialties Manufacturing Association (Blue Book, McNair-Dorland Co., N.Y. 1954; pages 243–244, 261) under controlled conditions of 80±5° F. and 50±5 percent relative humidity, were the test insects. The flies were immobilized by anesthetizing them with carbon dioxide. Twenty-five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty-four hours, at a temperature of 80±5° F. and at a relative humidity of 50±5 percent. Flies which showed no sign of movement on prodding were considered dead.

NEMATOCIDE TEST

The test organism used was the infective migratory larvae of the root-knot nematode, *Meloidogyne incognita* var. *acrita*, reared in the greenhouse on roots of cucumber plants. Infected plants were removed from the culture, and the roots were chopped very finely. A small amount of this inoculum was added to a pint jar containing approximately 180 cc. of soil. The jars were capped and incubated for one week at room temperature. During this period eggs of the nematode were hatched, and the larval forms migrated into the soil.

Ten ml. of the test formulation were added to each of the two jars for each dosage tested. Following the addition of chemical, the jars were capped, and the contents thoroughly mixed on a ball mill for 5 mixtures.

The test compounds were formulated by a standard procedure of solution in acetone addition of an emulsifier, and dilution with water. Primary screening tests were conducted at 3.33 m.g. of the test compound per jar.

The jars were left capped at room temperature for a period of 48 hours, and the contents then transferred to 3 inch pots. Subsequently, the pots were seeded to cucumber as an indicator crop and placed in the greenhouse where they were cared for in the normal fashion for approximately 3 weeks.

The cucumber plants were then taken from the pots, the soil removed from the roots, and the amount of galling visually rated.

The results of these tests are set forth in Table I below. In these tests the pesticidal activity of the compounds at the indicated dosage rate against aphid, Southern Armyworm, Bean Beetle and housefly was rated as follows:

A = excellent control
B = partial control
C = no control at 500 ppm

In the test for activity against nematodes activity was rated as follows:

1 = severe galling, equal to untreated plants
2 = moderate galling
3 = light galling
4 = very light galling
5 = no galling, perfect control
A dashed line indicates that no test was conducted.

TABLE I $$CH_3-C(SCH_3)=N-O-C(=O)-N(CH_3)-S-N(CH_3)-C(=O)-O-\text{Ar}(R, R_1, R_2)$$

| Compound | R | $R_1$ | $R_2$ | Melting Point (°C.) | Aphids | Southern Armyworm | Southern Armyworm (egg) | Mexican Bean Beetle | Housefly | Root-Knot Nematode |
|---|---|---|---|---|---|---|---|---|---|---|
| 1 | H | 3-C(=O)—CH₃ | H | 98–99.5 | A | A | A | A | A | 5 |
| 2 | H | 4-C(=O)—CH₃ | H | 138–39 | A | A | A | A | A | 5 |
| 3 | H | 3-CH(=O) | H | amorphous* solid | A | A | — | A | A | 1 |
| 4 | H | 4-COOH | H | 180–83 | B | A | — | A | A | — |
| 5 | 2-OCH₃ | 4-CH(=O) | H | 140Δ42 | A | A | B | A | A | 2 |
| 6 | H | 4-C(=O)—C₆H₅ | H | 80–82 | A | A | A | A | A | 4 |

TABLE I-continued $$CH_3-C(SCH_3)=N-O-C(=O)-N(CH_3)-S-N(OCH_3)-C(=O)-O-\text{Ar}(R, R_1, R_2)$$

| Compound | R | $R_1$ | $R_2$ | Melting Point (°C.) | Aphids | Southern Armyworm | Southern Armyworm (egg) | Mexican Bean Beetle | Housefly | Root-Knot Nematode |
|---|---|---|---|---|---|---|---|---|---|---|
| 7 | 3-$CH_3$ | 4-C(=O)-$CH_3$ | H | 90–93 | A | A | A | A | A | 5 |
| 8 | H | 2-C(=O)-H | H | oil** | A | A | B | A | A | 4 |
| 9 | 4-$CH_3$ | 2-C(=O)-$CH_3$ | 5-$CH_3$ | 149–51 | A | A | A | A | A | 1 |
| 10 | 5-$OCH_3$ | 2-C(=O)-$C_6H_5$ | H | 103–05 | A | A | A | A | A | 5 |

*Formula: $C_{14}H_{17}N_3O_5S_2$ Calculated: C-45.27 H-4.61 N-11.31 Found: C-44.73 H-4.79 N-11.02
**Formula: $C_{14}H_{17}N_3O_5S_2$ Calculated: C-45.27 H-4.61 N-11.31 Found: C-44.69 H-4.75 N-11.40

It will be understood that the insect species and other pests employed in the above tests are merely representative of a wide variety of pests that can be controlled by use of the novel compounds of this invention.

Selected species of the new compounds were evaluated for their residual pesticidal activity in soil. For comparative purposes, similar tests were run on compounds not possessing the ketone or aldehyde structure of the new compounds and on methomyl. The residual activity test were conducted using five to seven-day old housefly adults (*Musca domestica*).

The soil mixture used was one part agricultural soil and three parts sand. The agricultural soil was stored in plastic bags in a freezer, immediately after removal from the field. This was done to reduce microbial multiplication. Two weeks prior to use, the soil was thawed and held at room temperature to allow microbial population to equilibrate. The sand and soil were sifted to remove clumps and debris and were then blended by rolling on a roller mill in a closed metal container. The moisture level was adjusted to 15% by weight.

The concentration in the soil of the compound to be tested was four times the amount (in parts per million) necessary to achieve a mortality rate of 50% on contact with the soil ($LD_{50}$). This is in accordance with the procedure developed by C. R. Harris of the Research Institute, Canadian Department of Agriculture, London, Ontario. Such procedure is disclosed in "Biological Activity of Chloropyrifos, Chlorpyrifor-Methyl, Phorate, and Counter ® in Soil", *The Canadian Entomologist*, Vol. 109, pp. 1115–1120 (August 1977); and in "Laboratory Studies on the Persistance of Biological Activity of Some Insecticides in Soils", *Journal of Economic Entomology*, Vol. 62, No. 6, pp. 1437–1441 (December 1969).

An appropriate amount of compound was dissolved in an acetone—Triton solution and was diluted with water. Five mililiters of the formulated chemical was applied to four ounces of soil mixture and rolled in a 16-ounce glass jar to blend the compound evenly with the soil. Ten mililiters of granular cane sugar was then mixed thoroughly with the treated soil in an eight-ounce plastic container.

Twenty-five housefly adults, anesthetized with $CO_2$, were then transferred to the soil and were covered with a perforated plastic lid. The test containers were held for 24 hours in a constant environment at a temperature of $80\pm5°$ F. and a relative humidity of $50\pm F.°$. Mortality was based on the ability of the fly to move in a normal manner without spinning.

The above process was repeated on treated soil which had been incubated at 25° C. and 90% relative humidity for 1, 4, 6 and 8 weeks after initial exposure. This was necessary because the soil is incubated without sugar, sugar being added at the time of reinfestation. For this reason, appropriate volumes of soil had to be treated at the start of the soil test to last for the expected residual period.

The results obtained for the soil residuary test are summarized in Table II below.

TABLE II

Comparative Residual Effect In Soil $$CH_3-\underset{\underset{CH_3S}{|}}{C}=N-O-\overset{O}{\underset{||}{C}}-\underset{\underset{CH_3}{|}}{N}-S-\underset{\underset{CH_3}{|}}{N}-\overset{CH_3O}{\underset{||}{C}}-O-\text{(phenyl with }R_1, R_2, R_3\text{)}$$

| Compound | $R_1$ | $R_2$ | $R_3$ | $LD_{50}$ | Residual Concentration 0 (weeks) | 1 | 4 | 8 | Residual Activity (weeks) |
|---|---|---|---|---|---|---|---|---|---|
| 1 | 3-C(=O)-CH$_3$ | H | H | 360 | 1440 | 100 | 100 | 50 | 30 | 4–8 |
| 3 | 3-CH$_3$ | H | H | 370 | 1480 | 100 | 100 | 73 | 40 | 4–8 |
| A | 3-CH$_3$ | H | H | 315 | 1260 | 100 | 100 | 23 | — | less than 4 |
| B | 3-CH$_3$ | 4-CH$_3$ | 5-CH$_3$ | 178 | 710 | 100 | 100 | 0 | — | less than 4 |
| Methomyl* | — | — | — | 97 | 380 | 100 | 100 | 15 | — | less than 4 |

*methyl N—[[(methylamino)carbonyl]oxy]ethanimidothioate

These results demonstrate the improved residual effects of applicants' novel compound vis-a-vis other structurally similar pesticides known in the art. Compounds A and B are among those disclosed in U.S. Application Ser. No. 079,893 filed on Sept. 28, 1979 (D-10577-2) while methomyl is a well known commercial pesticide.

Several species of the novel compounds were tested for their phytotoxic effects. Two flats of each species of plants to be tested were planted 8–14 days before testing and grown at greenhouse conditions. One flat was sprayed with the chemical to be tested at the rate of eight pounds per acre while the other control flat was sprayed with solvent only. The results of such testing were recorded approximately two weeks after treatment and are reproduced in Table III below.

Numerical ratings from "0" to "10" are used to designate the degree of activity. A rating of zero (0) indicates that the compounds had no visible effects on that plant species.

TABLE III

PHYTOTOXICITY RESULTS $$H_3C-\underset{\underset{SCH_3}{|}}{C}=NO-\overset{O}{\underset{||}{C}}-\underset{\underset{CH_3}{|}}{N}-S-\underset{\underset{CH_3}{|}}{N}-\overset{O}{\underset{||}{C}}-O-\text{(phenyl with R)}$$

| R | Snapbean | Sorghum | Cucumber | Marigold | flax |
|---|---|---|---|---|---|
| 2-CH=O | 0 | 0 | 0 | 0 | 0 |
| 3-C(=O)CH$_3$ | 0 | 0 | 0 | 0 | 0 |
| 2-C(=O)CH$_3$ | 0 | 0 | 0 | 0 | 0 |

The compounds contemplated in this invention may be applied as insecticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desireable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents, for example, the condensation products of alkylene oxides with phenol and organic acids, alkyl aryl sulfonates, complex ether alcohols, quaternary ammonium compounds, and the like may be employed for this purpose.

In the preparation of wettable powder or dust or granualted compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied in amounts of from 1 to 200 gallons or more of liquid carrier and/or diluent or in from about 5 to 500 pounds of inert solid carrier and/or diluent per acre. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

In addition to their increased residual effects in the soil, the pesticides contemplated herein prevent attack by insects and nematodes upon plants or other material to which they are applied. With respect to plants, they have a high margin of safety in that when used in sufficient amount to kill or repel the insects they do not burn or injure the plant. The novel pesticides resist weathering, including wash-off caused by rain, decomposition by ultra-violet light, oxidation, and hydrolysis in the presence of moisture or, at least, such decomposition, oxidation, and hydrolysis as would materially decrease the desirable pesticidal characteristic of the toxicants or impart undesirable characteristics, for instance phytotoxicity, to the toxicants. The toxicants are compatible with other constituents of the spray schedule, and they may be used in the soil, upon the seeds, or the roots of plants without injuring either the seeds or roots of plants. Mixtures of the active compounds may be employed if desired as well as combinations of the active compounds of this invention with other biologically active compounds.

What is claimed is:

1. A compound of the formula:

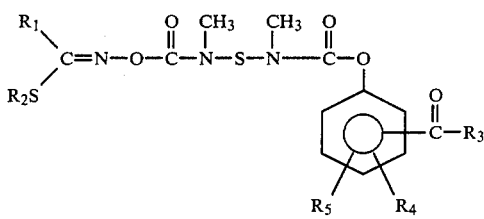

wherein:
$R_1$ and $R_2$ independently are $C_{1-4}$ alkyl
$R_3$ is hydrogen, $C_{1-4}$ alkyl or a phenyl group; and
$R_4$ and $R_5$ independently are hydrogen, $C_{1-4}$ alkyl or alkoxy.

2. A compound of the formula:

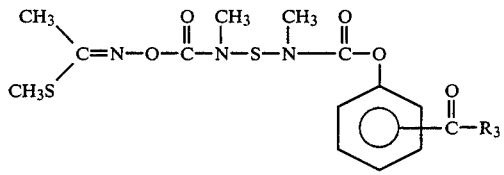

wherein $R_3$ is hydrogen, $C_{1-4}$ alkyl or a phenyl group.

3. S-Methyl-N-[[[N'-[[N''-[(2-formylphenoxy)carbonyl]-N''-methylaminosulfenyl]]-N'-methylcarbamoyloxy]]]thioacetimidate.

4. S-Methyl-N-[[[N'-[[N''-[(3-formylphenoxy)carbonyl]-N''-methylaminosulfenyl]]-N'-methylcarbamoyloxy]]]thioacetimidate.

5. S-Methyl-N-[[[N'-[[N''-[(3-acetylphenoxy)carbonyl]-N''-methylaminosulfenyl]]-N'-methylcarbamoyloxy]]]thioacetimidate.

6. An insecticidal or nematocidal composition which comprises an acceptable carrier and an insecticidally or nematocidally effective amount of a compound of the formula:

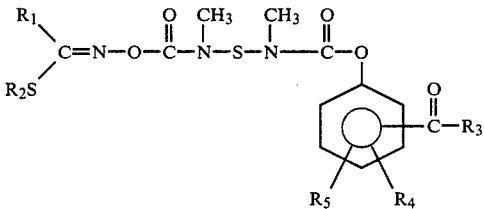

wherein:
$R_1$ and $R_2$ independently are $C_{1-4}$ alkyl
$R_3$ is hydrogen, $C_{1-4}$ alkyl or a phenyl group; and
$R_4$ and $R_5$ independently are hydrogen, $C_{1-4}$ alkyl or alkoxy.

7. An insecticidal or nematocidal composition which comprises an acceptable carrier and an insecticidally or nematocidally effective amount of a compound of the formula:

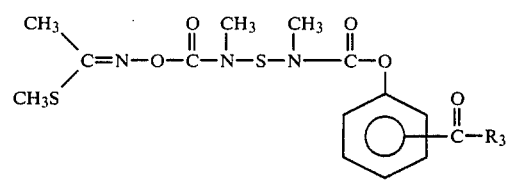

wherein $R_3$ is hydrogen, $C_{1-4}$ alkyl or alkoxy.

8. The composition of claim 7 wherein the insecticidal or nematocidal compound is S-Methyl-N-[[[N'-[[N''-[(2-formylphenoxy)carbonyl]N''-methylaminosulfenyl]]-N'-methylcarbamoyloxy]]]thioacetimidate.

9. The composition of claim 7 wherein the insecticidal, miticidal or nematocidal compound is S-Methyl-N-[[[N'-[[N''-[(3-formylphenoxy)carbonyl]N''-methylaminosulfenyl]]-N'-methylcarbamoyloxy]]]thioacetimidate.

10. The composition of claim 7 wherein the insecticidal or nematocidal compound is S-Methyl-N-[[[N'-[[N''-[(3-acetylphenoxy)carbonyl]-N''-methylamiosulfenyl]]-N'-methylcarbamoyloxy]]]thioacetimidate.

11. A method of controlling insects and nematodes which comprises subjecting them to an insecticidally or nematocidally effective amount of a compound of the formula:

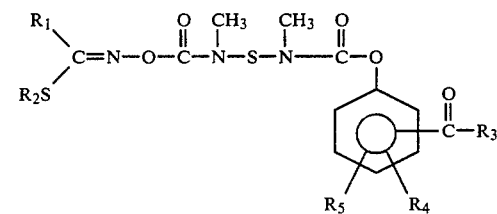

wherein:
$R_1$ and $R_2$ independently are $C_{1-4}$ alkyl
$R_3$ is hydrogen, $C_{1-4}$ alkyl or a phenyl group; and
$R_4$ and $R_5$ independently are hydrogen, $C_{1-4}$ alkyl or alkoxy.

12. A method of controlling insects and nematodes which comprises subjecting them to an insecticidally or nematocidally effective amount of a compound of the formula:

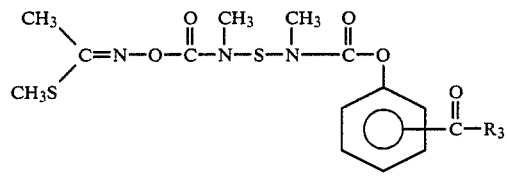

wherein $R_3$ is hydrogen, $C_{1-4}$ alkyl or a phenyl group.

13. The method of claim 12 wherein the insecticidal and nematocidal compound is S-Methyl-N-[[[N'-[[N''-

[(2-formylphenoxy)carbonyl]N''-methylaminosulfenyl]]-N'-methyl-carbamoyloxy]]]thioacetimidate.

14. The method of claim 12 wherein the insecticidal and nematocidal compound is S-Methyl-N-[[[N'-[[N''-[(3-formylphenoxy)carbonyl]N''-methylaminosulfenyl]]-N'-methylcarbamoyloxy]]]thioacetimidate.

15. The method of claim 12 wherein the insecticidal and nematocidal compound is S-Methyl-N-[[[N'-[[N''-[(3-acetylphenoxy)carbonyl]N''-methylaminosulfenyl]]-N'-methylcarbamoyloxy]]]thioacetimidate.

* * * * *